United States Patent
Vollbrecht et al.

(10) Patent No.: US 7,001,349 B2
(45) Date of Patent: Feb. 21, 2006

(54) ORTHOPEDIC SPLINT

(75) Inventors: Matthias Vollbrecht, Herzberg (DE); Helmut Wagner, Duderstadt (DE); Klaus Lidolt, Duderstadt (DE); Andreas Mühlenberend, Leipzig (DE)

(73) Assignee: Otto Bock Healthcare GmbH, Duderstadt (DE)

(*) Notice: Subject to any disclaimer, the term of this patent is extended or adjusted under 35 U.S.C. 154(b) by 0 days.

(21) Appl. No.: 10/917,542

(22) Filed: Aug. 12, 2004

(65) Prior Publication Data

US 2005/0038364 A1    Feb. 17, 2005

(30) Foreign Application Priority Data

Aug. 12, 2003 (DE) ............................... 103 37 332

(51) Int. Cl.
*A61F 5/00* (2006.01)

(52) U.S. Cl. .............................. 602/5; 602/12; 602/16; 602/23

(58) Field of Classification Search ............... 602/5, 602/12, 16, 20, 23, 26; 623/27, 39
See application file for complete search history.

(56) References Cited

U.S. PATENT DOCUMENTS

| 58,403 A | * | 10/1866 | Goodwin ............ 602/16 |
| 575,199 A | * | 1/1897 | Autenrieth ............ 602/16 |
| 1,336,695 A | | 4/1920 | Groms |
| 1,366,576 A | * | 1/1921 | Maddox ............ 602/5 |
| 1,381,290 A | | 6/1921 | Diadul, Jr. |
| 1,418,283 A | | 6/1922 | Cameron |
| 1,559,339 A | * | 10/1925 | Masland ............ 602/5 |
| 1,885,448 A | | 11/1932 | Jones |
| 2,260,216 A | | 10/1941 | Doyle |
| 3,799,158 A | | 3/1974 | Gardner |
| 3,875,935 A | | 4/1975 | Drew |
| 3,902,482 A | | 9/1975 | Taylor |
| 4,241,730 A | | 12/1980 | Helfet |
| 4,256,097 A | | 3/1981 | Willis |
| 4,419,991 A | * | 12/1983 | Lee ............ 602/16 |
| 4,428,369 A | | 1/1984 | Peckham et al. |
| 4,463,751 A | | 8/1984 | Bledsoe |
| 4,485,808 A | * | 12/1984 | Hepburn ............ 602/5 |
| 4,632,098 A | | 12/1986 | Grundei et al. |
| 4,665,905 A | * | 5/1987 | Brown ............ 602/16 |
| 4,686,969 A | | 8/1987 | Scott |
| 4,807,609 A | * | 2/1989 | Meals ............ 602/20 |

(Continued)

FOREIGN PATENT DOCUMENTS

DE            357243          8/1922

(Continued)

*Primary Examiner*—Henry Bennett
*Assistant Examiner*—Amanda Wieker
(74) *Attorney, Agent, or Firm*—Faegre & Benson, LLP

(57) ABSTRACT

An orthopedic splint, which, as part of an orthosis, is intended to bear on a part of the body, can be used with different configurations. The splint consists of two round rods (2, 3) which are arranged approximately in a plane (9) and whose ends on both sides are inserted rotatably in round seats (8) of two endpieces (1, 4). Both round rods (2, 3) are designed with at least one angled part (5, 6) in the plane (9). The round seats (8) of an endpiece (1, 4) form an acute angle with respect to one another and are designed with an excess dimension relative to the inserted end so that, by rotating the round rods (2, 3), different relative angles extending out from the plane (9) can be set between the endpieces (1, 4) in two end settings.

26 Claims, 2 Drawing Sheets

U.S. PATENT DOCUMENTS

| | | |
|---|---|---|
| 4,817,588 A | 4/1989 | Bledsoe |
| 4,821,707 A | 4/1989 | Audette |
| 4,854,308 A | 8/1989 | Drillio |
| 4,881,532 A | 11/1989 | Borig et al. |
| 4,962,760 A | 10/1990 | Jones |
| 5,002,045 A | 3/1991 | Spademan |
| 5,056,509 A | 10/1991 | Swearington |
| 5,086,760 A | 2/1992 | Neumann et al. |
| 5,107,824 A | 4/1992 | Rogers et al. |
| 5,111,808 A * | 5/1992 | Meals .................. 602/23 |
| 5,131,385 A | 7/1992 | Kuehnegger et al. |
| 5,232,435 A * | 8/1993 | Leibinsohn ............ 602/16 |
| 5,261,873 A * | 11/1993 | Bremer et al. ......... 602/32 |
| 5,302,169 A | 4/1994 | Taylor |
| 5,342,288 A * | 8/1994 | Lee et al. .............. 602/5 |
| 5,400,806 A | 3/1995 | Taylor |
| D407,490 S * | 3/1999 | Zepf et al. ............ D24/155 |
| 6,565,523 B1 | 5/2003 | Gabourie |

FOREIGN PATENT DOCUMENTS

| | | |
|---|---|---|
| DE | 520 959 | 3/1931 |
| DE | 2 301 746 | 6/1973 |
| DE | 2 239382 | 2/1974 |
| GB | 2 136 294 | 3/1983 |
| GB | 2 163 352 | 8/1984 |
| WO | WO 94/15555 | 12/1993 |
| WO | WO99/59507 | 11/1999 |

* cited by examiner

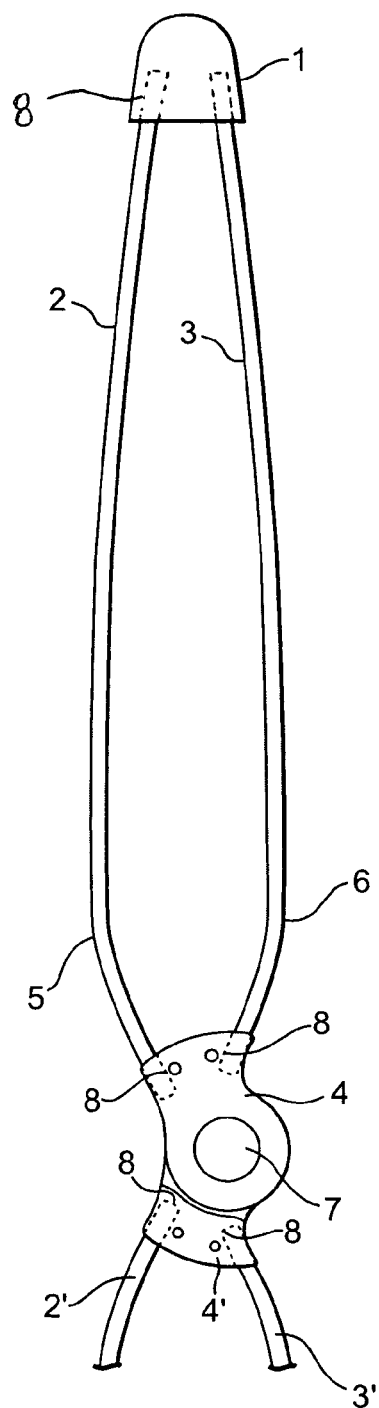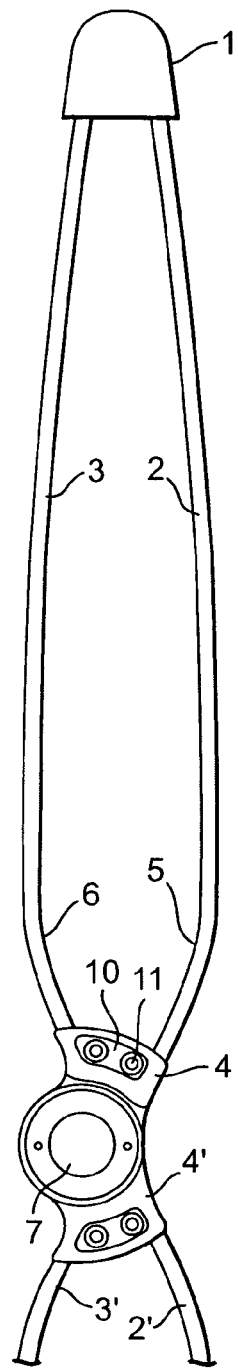

ORTHOPEDIC SPLINT

CROSS-REFERENCE TO RELATED APPLICATION(S)

This application claims priority to German patent application no. 103 37 332.2, filed on Aug. 12, 2003.

TECHNICAL FIELD

The invention relates to an orthopedic splint which, as part of an orthosis, is intended to bear on a part of the body.

BACKGROUND

For supporting parts of the body, in particular the limbs, with an orthopedic splint, it is in many cases necessary to adapt the splint to the part of the body in order to achieve the desired support. For this purpose, it is known to produce an orthopedic splint from a flat metal which is plastically deformable in order to provide the desired configuration. A disadvantage of this is that the deformability limits the stability of the splint, and the latter cannot, for example, be used as part of an orthosis loaded by the weight of the body.

It is therefore known for such splints, particularly as part of orthotic devices, to be produced specifically for the intended case of use, which entails considerable costs. Thus, for example, orthotic devices which are in principle identical are produced in different configurations depending on whether they are provided for correction of genu valgum, also known as knock knee, or for correction of the reverse condition, genu varum, also known as bow leg. Thus, not only is production more expensive, but also storage.

The object of the invention is to design an orthopedic splint of the type mentioned at the outset in such a way that it is easy to produce and requires less outlay for its storage.

SUMMARY

To achieve this object, an orthopedic splint of the type mentioned at the outset is such that the splint consists of two round rods which are arranged approximately in a plane and whose ends on both sides are inserted rotatably in round seats of two end pieces. Both round rods are designed with, in each case, at least one angled part in the plane. The round seats of an endpiece form an acute angle with respect to one another. The round seats are designed with an excess dimension relative to the inserted end so that, by rotating the round rods, different relative angles extending out from the plane can be set between the endpieces in two end settings.

The orthopedic splint according to the invention thus allows the endpieces to be set at an angle out from the plane with respect to one another, which angle is preferably a maximum of 5°. This angled setting is possible in both directions since the arrangement according to the invention permits, in particular, two stable end settings in which the orthosis can be loaded while remaining stable. Because of the two end settings, the orthopedic splint according to the invention is suitable in particular for the construction of an orthosis for correction of genu valgum or genu varum. One end setting is suitable for correction of genu valgum and the other end setting is suitable for correction of genu varum.

The mode of function of the orthopedic splint according to the invention is based on the fact that the round rods are mounted in the round seats of the endpieces so as to be rotatable about a respective center axis of the round seats. The rotation of the round rods in the round seats lead to a change in the angled setting on account of the angled part. Therefore, because of the excess dimension, only slight rotations of the round rods in the round seat are necessary until one of the end settings is reached. The rotation of the round rods corresponds to a setting of a relative angle between the endpieces, i.e., an angled setting of the endpieces out from the (starting) plane. In one end setting, the angled setting extends out from one side from the plane, while, in the other end setting, it extends out from the other side of the plane. The respective setting of the splint in one of the end settings or an intermediate setting is suitably fixed, preferably by means of a clamp device.

In a preferred embodiment, which is suitable in particular for adaptation to the contour of the leg, the angled parts of the round rods are situated near one of the endpieces. Thus, the angle out from the plane is formed near one of the endpieces, which can be particularly appropriate for a thigh splint.

The angled parts of the two round rods are preferably designed as mirror images with respect to one another. This ensures that the shaping caused by the angled setting takes place in the frontal plane and does not entail any twisting of the splint.

For stability and weight reasons, the round rods can preferably be formed by tubes.

If at least one of the endpieces of the splint is designed as part of a pivot hinge, the splint can readily be used for an orthosis with a pivot hinge. A preferred application of the splint according to the invention consists in the formation of an orthosis which is used for correction of genu valgum or genu varum. For this purpose, two splints are preferably connected to one another via a pivot hinge for placement at the knee joint.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 shows a front view of an illustrative embodiment of an orthopedic splint as part of an orthosis for correction of genu valgum or genu varun.

FIG. 2 shows a rear view of the splint according to FIG. 1.

DETAILED DESCRIPTION

Figures 3A, 3B, 3C:
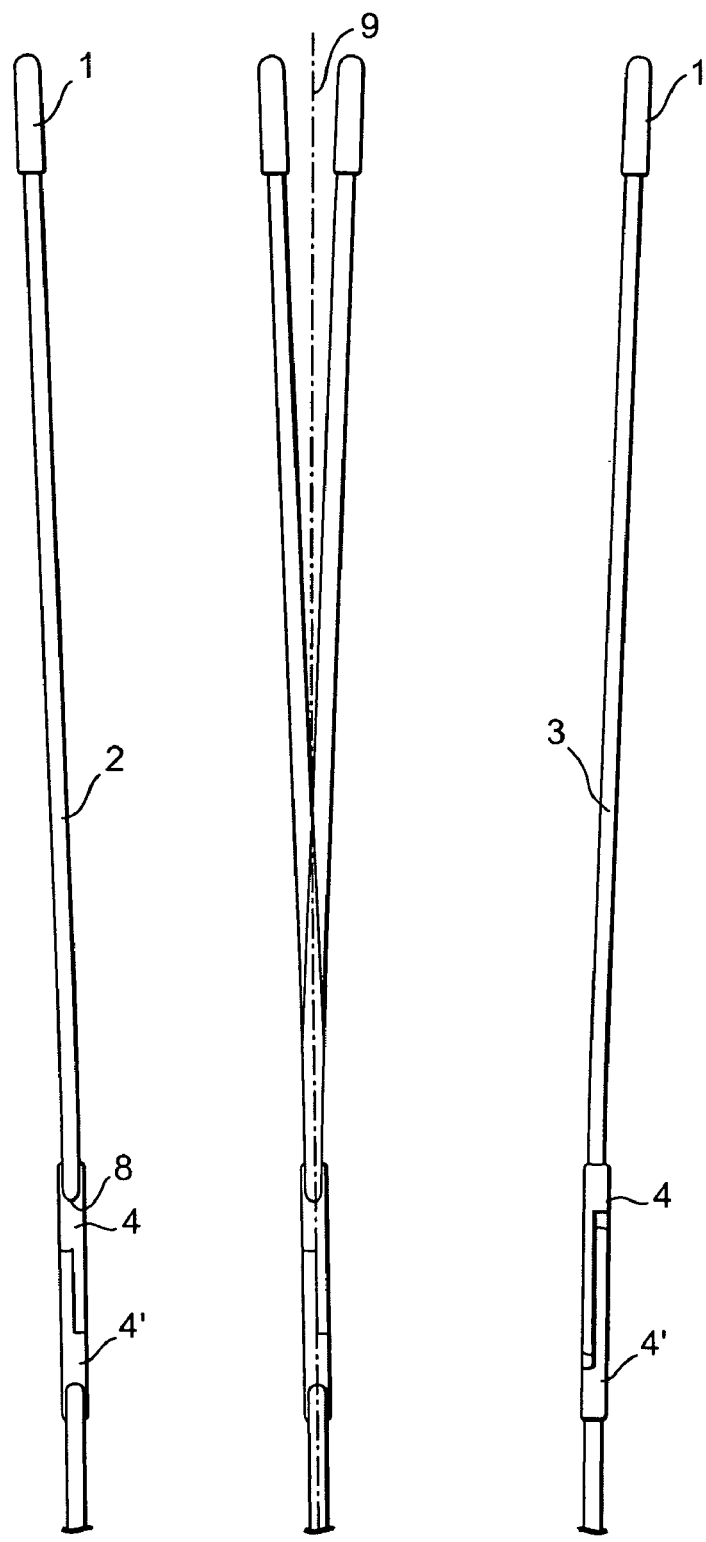
FIGS. 3a–c show a side view of the orthosis according to FIG. 1 viewed in a first configuration, viewed in a second configuration, and, diagrammatically, with both possible configurations viewed relative to a starting plane.

The orthopedic splint shown in the drawings in FIGS. 1, 2 and 3a–c, consists of a first endpiece 1 having two round seats 8 in which ends of a first round rod 2 and of a second round rod 3 are received. The round seats 8 form an acute angle with one another and are oriented symmetrically with respect to a center axis of the endpiece 1, so that the two round rods 2, 3, starting from the endpiece 1, point away from one another at the same angles with respect to the center axis and with initially rectilinear portions. The round rods 2, 3 merge with a slight curvature into almost parallel portions until presenting, in proximity to a second endpiece 4, angled parts 5, 6 via which the round rods 2, 3, with their ends running toward one another and toward the second endpiece 4, are now inserted into said second endpiece 4. The second endpiece 4 is at an angle to the center axis of the first endpiece 1, so that the ends of the round rods 2, 3, which are themselves designed symmetrically to one another, are at different angles to a center axis of the second endpiece 4. For adaptation to the oblique setting of the second endpiece 4, the first round rod 2 is longer than the second round rod 3 in the area of its end pointing to the second endpiece 4.

The second endpiece 4 is designed as part of a pivot hinge 7 via which a further second endpiece 4' of a further orthopedic splint is arranged rotatably with respect to the second endpiece 4 of the first splint. Corresponding round rods 2', 3' are inserted into the endpiece 4'. The other end of round rods 2' and 3' would preferably be inserted into a further first endpiece 1', which is not shown.

FIG. 3a shows a side view of the splint according to FIG. 1, so that the round rod 2 can be seen. The round seat 8 can also be seen in the second endpiece 4 for the end of the round rod 2. In the setting shown in FIG. 3a, the round rods 2, 3 are turned so that they are bent to the left in the view in FIG. 3a and to the right in the view in FIG. 3b (rear view of the round rod 3) by a small angle of about 3°. This angle may vary, but is preferably no greater than about 5°.

FIG. 3c illustrates a center plane 9 in which the round rods 2, 3 and the endpieces 1, 4 are essentially arranged. By virtue of the design according to the invention, two stable end settings are possible, which are both shown in FIG. 3c with each having slightly angled settings that are symmetrical with respect to the plane 9. The respective setting can be fixed with a clamp device 10 which, by means of clamping screws 11, suppresses the rotatability of the round rods 2, 3.

The splint shown is preferably part of an orthosis with two splints and the pivot hinge 7. This orthosis is particularly suitable for correction of genu valgum and genu varum, when the pivot hinge 7 is situated at the level of the patient's knee joint. The end settings shown in FIG. 3c illustrate the possible adjustment of the splint to adapt it to the contour of the leg. Moreover, prestressing can also be generated in the orthosis. This provides load relief, which can be made use of for genu valgum or genu varum.

In an alternative embodiment, an orthopedic splint is formed from a pair of elongated members 2, 3 each having first and second ends. The first ends of the members 2, 3 are coupled together at a first end connector 1 and the second ends of the members 2, 3 are couple together at a second end connector 4. The same type of end connector 1, 4 may be used to couple both ends of the members 2, 3, or, as shown in the Figures, different types of end connectors 1, 4 may be used to couple the ends of the members 2,3.

Each end connector 1, 4 includes a pair of apertures 8 formed at an acute angle with respect to each other, such that each aperture has a center axis with the axes of the two apertures configured at an acute angle relative to each other. Each aperture 8 is configured to receive one of the elongated members 2, 3 and provide for the reorientation of the member within the aperture 8. As described above, in a preferred embodiment, the member 2, 3 is a round rod or tube and the aperture is a round seat, such that the round rod or tube may be rotated within the round seat in order to reorient the rod or tube with respect to the end connector. However, other member cross-sectional shapes may also be provided with compatibly shaped apertures, for example, square, star-shaped, octagonal and others. Thus, these members may be reoriented in a discrete number of positions relative to the apertures. In addition, a restraining mechanism 10, 11 may be provided to limit the movement of each member 2, 3 within its aperture 8. The mechanism 10, 11 may include, but is not limited to, a clamp or a set screw.

Each elongated member 2, 3 is provided with a bend 5, 6 positioned at a predetermined location along the length of the member 2, 3. In one embodiment, the bend 5, 6 is located near the first end connector 1 and, in another embodiment, the bend 5, 6 is located near the second end connector 4. Alternatively, the bend 5, 6 may be located anywhere along the length of the member 2, 3. The location of the bend 5, 6 is preferably determined by the desired use of the splint.

As described above, reorientation of the bent members 2, 3 results in a plurality of settings relative to the first and second end connectors 1, 4. These settings include a configuration of the splint with the bent members 2, 3 angling out of a center plane 9, as shown in FIG. 3c. Reorientation of the members 2, 3 within the apertures 8 then results in a different setting. At least some of the settings that are possible, based on the configurations of the members and apertures, angle the members 2, 3 out of the plane 9 in a first direction and others of the settings angle the members 2, 3 out of the plane 9 in an opposite direction. In one embodiment, the degree of angle out of the plane 9 may be up to a maximum of 5 degrees.

Multiple splints of the type described above may be coupled together to form an orthosis. In a preferred embodiment, at least one of the first and second end connectors 1, 4 is configured as a component of a pivoting hinge 7. Two splints are then combined together at the hinge 7 to form a leg orthosis. This orthosis may then be adapted to treat various conditions by use of the different settings available for the splints. As stated above, two preferred treatment configurations are for genu valgum and genu varum.

Although the present invention has been described with reference to exemplary embodiments, persons skilled in the art will recognize that changes may be made in form and detail without departing from the spirit and scope of the invention.

We claim:

1. An orthopedic splint intended to bear on a part of the body, the splint comprising:
two round rods arranged generally in a plane and having first and second ends, each round rod being configured with at least one angled part in the plane; and
first and second endpieces, each including two round seats in which the two round rods are rotatably received at their first and second ends, respectively, the round seats of each endpiece forming an acute angle with respect to one another, and the round seats being configured with an excess dimension relative to the received first or second end of each round rod so that, by rotating the round rods, two end settings are achievable with respect to the endpieces, each having a different relative angle extending out from the plane.

2. The orthopedic splint as claimed in claim 1, wherein the angled parts of the round rods are situated near one of the first and second endpieces.

3. The orthopedic splint as claimed in claim 1, wherein the angled parts of the two round rods are configured as mirror images with respect to one another.

4. The orthopedic splint as claimed in claim 1, wherein the relative angle between the first and second endpieces corresponds to an angle extending out from the plane of a maximum of about 5°.

5. The orthopedic splint as claimed in claim 1, wherein the round rods are tubes.

6. The orthopedic splint as claimed in claim 1, wherein at least one of the first and second endpieces is configured as a component of a pivot hinge.

7. The orthopedic splint as claimed in claim 6, wherein the splint comprises part of an orthosis configured to correct genu valgum or genu varum.

8. The orthopedic splint as claimed in claim 1, wherein the splint comprises part of an orthosis configured to correct genu valgum or genu varum.

9. An orthosis comprising:
first and second splints, each splint including:
two round rods arranged generally in a plane and having first and second ends, each round rod being configured with at least one angled part in the plane; and
first and second endpieces, each including two round seats in which the two round rods are rotatably received at the first and second ends, respectively, the round seats of each endpiece forming an acute angle with respect to one another, and the round seats being configured with an excess dimension relative to the received first or second end of each round rod so that, by rotating the round rods, two end settings are achieved with respect to the endpieces, each having a different relative angle extending out from the plane; and
a pivot hinge connected to the first and second splints.

10. The orthosis of claim 9, wherein at least one of the first and second endpieces of at least one of the first and second splints is configured as a component of the pivot hinge.

11. The orthosis of claim 9, wherein at least one of the first and second endpieces of each of the first and second splints is configured as a component of the pivot hinge.

12. The orthosis of claim 11, wherein the angled parts of the round rods are situated near the at least one of the first and second endpieces of each of the first and second splints configured as a component of the pivot hinge.

13. The orthosis of claim 9, wherein the orthosis is configured to correct genu valgum or genu varum.

14. The orthosis of claim 13, wherein one of the two end settings is suitable for correcting genu valgum and the other one of the two end settings is suitable for correcting genu varum.

15. The orthosis of claim 9, wherein the angled parts of the round rods are situated near one of the first and second endpieces.

16. The orthosis of claim 9, wherein the angled parts of the two round rods are configured as mirror images with respect to one another.

17. The orthosis of claim 9, wherein the relative angle between the first and second endpieces corresponds to an angle extending out from the plane of a maximum of about 5°.

18. The orthosis of claim 9, wherein the round rods are tubes.

19. The orthosis of claim 9, wherein at least one of the first and second splints is prestressed.

20. The orthosis of claim 9, wherein the different relative angles of the two end settings extend out toward different sides of the plane.

21. An orthopedic splint comprising:
first and second elongated members each having first and second ends;
a first end connector coupled to the first ends of the first and second elongated members, such that each of the first and second members is reorientable with respect to the first end connector;
a second end connector coupled to the second ends of the first and second elongated members, such that each of the first and second members is reorientable with respect to the second end connector,
wherein the first and second elongated members are oriented within the first and second end connectors in a first setting in which one of the first and second end connectors angles out of a center plane in a first direction relative to the other of the first and second end connectors, and
wherein the first and second elongated members are reorientable within the first and second end connectors into a second setting in which one of the first and second end connectors angles out of a center plane in an opposite direction relative to the other of the first and second end connectors.

22. The orthopedic splint of claim 21, wherein at least one of the first and second members has a round cross-section.

23. The orthopedic splint of claim 21, wherein the first and second end connectors comprise first and second apertures configured to receive the first and second elongated members with the first and second elongated members reorientable within the first and second apertures.

24. The orthopedic splint of claim 21, wherein the first and second elongated members each included at least one bend.

25. The orthopedic splint of claim 21, wherein at least one of the first and second end connectors comprises a restraining mechanism configured to hold the first and second elongated members in a predetermined position.

26. The orthopedic splint of claim 21, wherein at least one of the first and second end connectors is configured as a component of a pivoting hinge.

* * * * *